US006172048B1

(12) United States Patent
Behr et al.

(10) Patent No.: US 6,172,048 B1
(45) Date of Patent: *Jan. 9, 2001

(54) COMPOSITION CONTAINING NUCLEIC ACIDS, PREPARATION AND USES

(75) Inventors: Jean-Paul Behr, Strasbourg; Barbara Demeneix, Paris; Daniel Scherman, Paris Cedex; Bertrand Schwartz, Maisons Alfort; Jean-Serge Remy, Strasbourg, all of (FR)

(73) Assignee: Aventis Pharma S.A. (FR)

( * ) Notice: Under 35 U.S.C. 154(b), the term of this patent shall be extended for 0 days.

This patent is subject to a terminal disclaimer.

(21) Appl. No.: 09/160,937

(22) Filed: Sep. 25, 1998

Related U.S. Application Data

(63) Continuation of application No. 08/666,308, filed as application No. PCT/FR95/00022 on Jan. 9, 1995, now Pat. No. 5,846,947.

(30) Foreign Application Priority Data

Jan. 10, 1994 (FR) .................................................. 94 00159

(51) Int. Cl.[7] .................................................. A61K 48/00
(52) U.S. Cl. .......................... 514/44; 435/320.1; 435/325; 435/455; 435/458; 536/23.1; 536/24.5; 424/450
(58) Field of Search .............................. 424/450; 435/455, 435/458, 320.1, 325; 514/44; 536/23.1, 24.5

(56) References Cited

U.S. PATENT DOCUMENTS

| 5,171,678 | * | 12/1992 | Behr et al. | 435/455 |
| 5,451,661 | * | 9/1995 | Wan et al. | 530/345 |
| 5,476,962 | * | 12/1995 | Behr et al. | 560/168 |
| 5,616,745 | * | 4/1997 | Behr et al. | 554/56 |
| 5,827,703 | * | 10/1998 | Debs et al. | 435/455 |
| 5,908,635 | | 6/1999 | Thierry . | |

OTHER PUBLICATIONS

Branch, TIBS 23, pp. 45–50, 1998.*

* cited by examiner

*Primary Examiner*—Scott D. Priebe
*Assistant Examiner*—Dave Trong Nguyen
(74) *Attorney, Agent, or Firm*—Connolly Bove Lodge & Hutz LLP

(57) ABSTRACT

The present invention relates to compositions comprising at least one nucleic acid and one lipopolyamine, and their utilisation in gene therapy, particularly for the transfer in vivo of nucleic acids.

30 Claims, No Drawings

COMPOSITION CONTAINING NUCLEIC ACIDS, PREPARATION AND USES

This application is a continuation of application Ser. No. 08/666,308, filed Jul. 10, 1996, now U.S. Pat. No. 5,846,947, which is a 371 of PCT/FR95/00022 filed Jan. 9,1995 with a claim to the priority of French application FR94/00159, filed Jan. 10, 1994.

The present invention relates to compositions based on nucleic acids, to their preparation and to their use. More particularly, it relates to compositions comprising at least one nucleic acid and one lipopolyamine and to their use in gene therapy, especially for the transfer of nucleic acids.

Gene therapy consists in correcting a deficiency or abnormality (mutation, aberrant expression, and the like) or in providing for the expression of a protein of therapeutic interest by introduction of genetic information into the affected cell or organ. This genetic information can be introduced either in vitro into a cell extracted from the organ, the modified cell then being reintroduced into the organism, or directly in vivo into the appropriate tissue. Various techniques have been described for the transfer of this genetic information, including various transfection techniques involving complexes of DNA and DEAE-dextran (Pagano et al., J. Virol., 1 (1967), 891), of DNA and nuclear proteins (Kaneda et al., Science, 243 (1989), 375), of DNA and lipids (Felgner et al., PNAS, 84 (1987), 7413) and of DNA and polylysine, the use of liposomes (Fraley et al., J. Biol. Chem., 255 (1980), 10431), and the like. More recently, the use of viruses as vectors for gene transfer has appeared as a promising alternative to these physicochemical transfection techniques. In this respect, various viruses have been tested for their ability to infect certain cell populations. In particular, retroviruses (RSV, HMS, MMS, and the like), the HSV virus, adeno-associated viruses and adenoviruses.

However, the techniques developed until now do not make it possible to satisfactorily resolve the difficulties related to the transfer of genes into cells and/or the organism. In particular, the problems related to the penetration of nucleic acid into cells are not completely solved. In fact, the polyanionic nature of nucleic acids prevents their passage through cell membranes. While it has been shown that naked nucleic acids are capable of passing through the plasma membrane of certain cell types in vivo (see especially Application No. WO 90/11092), transfection efficiency remains fairly low. Moreover, naked nucleic acids have a short plasma half-life, due to their degradation by enzymes and their removal by urinary routes. Moreover, while recombinant viruses make it possible to improve the efficiency of transfer of nucleic acids, their use presents certain risks such as pathogenicity, transmission, replication, recombination, transformation, immunogenicity, and the like.

The present invention introduces an advantageous solution to these various problems. The Applicant has in fact shown that certain compositions comprising a nucleic acid and a lipopolyamine can make possible the in vivo transfer of the said nucleic acid into a cell and/or organ with high efficiency and without toxicity. The compositions of the invention also make it possible to avoid the disadvantages related to the use of viral vectors (potential dangers, limited size of transferred gene, high cost, and the like).

The use of certain lipopolyamines for the in vitro transfection of cell cultures has already been described in the prior art. Thus, Application EP 394,111 describes the use of certain lipopolyamines for the in vitro transfection of cell lines. The article by Demeneix et al. (Int. J. Dev. Biol., 35 (1991), 481) likewise describes the use of a lipopolyamine (dioctadecylamidoglycylspermine, DOGS) for the in ovo transfection of nucleic acids. According to these documents, the lipopolyamines must be used under conditions such that the positive charges of the lipopolyamine/negative charges of the nucleic acid ratio is between 2 and 5 and preferably equal to 3 or 4. However, as shown in Examples 8 and 9 of the present application, none of the conditions described in these documents, surprisingly, makes possible the in vivo transfection of nucleic acids. Due to interaction with anionic macromolecules or with the extracellular matrix of the tissues, the particles formed under these conditions are in fact incapable of diffusing out of the site of application and thus of transferring any nucleic acid in vivo. Moreover, the preparation conditions described in these documents are not applicable to the production of pharmaceutical compositions containing significant amounts of nucleic acids. The Applicant has now shown that, under certain conditions, lipopolyamines can be used for the in vivo transfection of nucleic acids. More particularly, the Applicant has found that compositions comprising a nucleic acid and a lipopolyamine under conditions such that the positive charges of the lipopolyamine/negative charges of the nucleic acid ratio is less than or equal to 2 surprisingly make possible the in vivo transfection of the said nucleic acid with high efficiency. Moreover, the Applicant has developed certain conditions making possible the preparation of these pharmaceutical compositions incorporating significant amounts of nucleic acid. The pharmaceutical compositions of the invention thus constitute particularly advantageous tools for the administration and transfer of nucleic acids in vivo.

A first subject of the invention thus lies in a composition comprising at least one nucleic acid and one lipopolyamine in which the ratio R=positive charges of the lipopolyamine/negative charges of the nucleic acid is less than or equal to 2.

Within the meaning of the present invention, the term lipopolyamine denotes any amphiphilic molecule comprising at least one hydrophilic polyamine region and one lipophilic region. The cationically charged polyamine region of the lipopolyamines is capable of combining reversibly with the negatively charged nucleic acid. This interaction strongly compacts the nucleic acid. The lipophilic region makes this ionic interaction insensitive to the external medium, by covering the nucleolipid particle formed with a lipid layer.

Advantageously, the polyamine region of the lipopolyamines used in the context of the invention corresponds to the general formula

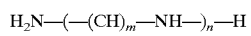

$$H_2N-(-(CH_2)_m-NH-)_n-H$$

in which m is an integer greater than or equal to 2 and n is an integer greater than or equal to 1, it being possible for m to vary between the different carbon groups included between two amines. Preferentially, m is between 2 and 6 inclusive and n is between 1 and 5 inclusive. Still more preferentially, the polyamine region is represented by spermine or an analogue of spermine which has retained its properties of binding to DNA.

The lipophilic region can be a saturated or unsaturated hydrocarbon chain, cholesterol, a natural lipid or a synthetic lipid capable of forming lamellar or hexagonal phases.

Use is advantageously made, in the context of the present invention, of the lipopolyamines as defined in Patent Application EP 394,111. This application also describes a process which can be used for the preparation of these lipopolyamines.

Use is particularly advantageously made, in the context of the invention, of dioctadecylamidoglycylspermine (DOGS) or of the 5-carboxyspermylamide of palmitoylphosphatidylethanolamine (DPPES).

In order to obtain an optimum effect of the compositions of the invention, the respective proportions of the polyamine and of the nucleic acid are preferably determined so that the positive charges of the lipopolyamine/negative charges of the nucleic acid ratio R is between 0.1 and 1.9 and more preferentially between 0.5 and 1.5.

In the compositions of the present invention, the nucleic acid can be both a deoxyribonucleic acid and a ribonucleic acid. There can be sequences of natural or artificial origin and especially genomic DNA, cDNA, MRNA, tRNA, rRNA, hybrid sequences or synthetic or semi-synthetic sequences. These nucleic acids can be of human, animal, plant, bacterial or viral origin and the like. They can be obtained by any technique known to those skilled in the art and especially by screening banks, by chemical synthesis or alternatively by mixed methods including chemical or enzymatic modification of sequences obtained by screening banks. They can moreover be incorporated in vectors, such as plasmid vectors.

As regards more particularly the deoxyribonucleic acids, they can be single or double stranded. These deoxyribonucleic acids can carry therapeutic genes, sequences regulating transcription or replication, antisense sequences, regions for binding to other cell components, and the like.

Within the meaning of the invention, therapeutic gene is understood to mean especially any gene coding for a protein product having a therapeutic effect. The protein product thus coded can be a protein, a peptide, and the like. This protein product can be homologous with respect to the target cell (that is to say, a product which is normally expressed in the target cell when the latter does not exhibit any pathology). In this case, the expression of a protein makes it possible, for example, to overcome an insufficient expression in the cell or the expression of an inactive or weakly active protein due to a modification or alternatively to overexpress the said protein. The therapeutic gene can also code for a mutant of a cell protein having an increased stability, a modified activity, and the like. The protein product can also be heterologous with respect to the target cell. In this case, an expressed protein can, for example, supplement or contribute to a deficient activity in the cell, making it possible for it to control a pathology or stimulate an immune response.

Mention may more particularly be made, among the therapeutic products within the meaning of the present invention, of enzymes, blood derivatives, hormones, lymphokines: interleukins, interferons, TNF, and the like (FR 9,203,120), growth factors, neurotransmitters or their precursors or enzymes for synthesis, trophic factors: BDNF, CNTF, NGF, IGF, GMF, aFGF, bFGF, NT3, NT5, HARP/pleiotrophin, and the like, apolipoproteins: ApoAI, ApoAIV, ApoE, and the like (FR 93 05125), dystrophin or a minidystrophin (FR 91 11947), the protein CFTR associated with mucoviscidosis, tumour-suppressor genes: p53, Rb, Rap1A, DCC, k-rev, and the like (FR 93 04745), genes coding for factors involved in clotting: Factors VII, VIII or IX, genes taking part in the repair of DNA, suicide genes (thymidine kinase, cytosine deaminase), and the like.

The therapeutic gene can also be an antisense sequence or gene whose expression in the target cell makes it possible to control cell MRNA transcription or gene expression. Such sequences can, for example, be transcribed in the target cell as complementary RNAs of cell mRNAs and thus block their translation into proteins, according to the technique described in Patent EP 140 308. The antisense sequences also comprise sequences coding for ribozymes, which are capable of selectively destroying target RNAs (EP 321,201).

As mentioned above, the nucleic acid can also comprise one or a number of genes coding for an antigenic peptide capable of generating an immune response in man or animals. In this specific embodiment, the invention thus makes possible the production either of vaccines or of immunotherapeutic treatments applied to man or to animals, especially against microorganisms, viruses or cancers. It can also concern antigenic peptides specific to Epstein-Barr virus, HIV virus, hepatitis B virus, (EP 185,573) or pseudorabies virus or alternatively specific to tumours (EP 259,212).

The nucleic acid preferentially also comprises sequences making possible the expression of the therapeutic gene and/or of the gene coding for the antigenic peptide in the desired cell or organ. These can be sequences which are naturally responsible for the expression of the gene under consideration when these sequences are capable of operating in the infected cell. They can also be sequences of different origin (responsible for the expression of other proteins, or even synthetic proteins). They can especially be promoter sequences of eukaryote or viral genes. For example, they can be promoter sequences resulting from the genome of the cell which it is desired to infect. Likewise, they can be promoter sequences resulting from the genome of a virus. In this respect, mention may be made, for example, of the promoters of the E1A, MLP, CMV or RSV genes and the like. These expression sequences can additionally be modified by addition of activation sequences, regulatory sequences, and-the like.

The nucleic acid can moreover also comprise, in particular upstream of the therapeutic gene, a signal sequence which directs the therapeutic product synthesised in the secretory pathways of the target cell. This signal sequence can be the natural signal sequence of the therapeutic product but it can also be any other functional signal sequence or an artificial signal sequence.

In another embodiment, the present invention relates to compositions comprising a nucleic acid, a lipopolyamine and an adjuvant capable of combining with the lipopolyamine/nucleic acid complex and of improving the transfecting ability. The Applicant has in fact shown that the transfecting ability of the lipopolyamines can be unexpectedly increased in the presence of certain adjuvants (lipids or proteins, for example) capable of combining with the lipopolyamine/nucleic acid complex. As is shown in Examples 4 to 7 of the present application, this improvement is displayed both in vitro and in vivo.

More preferentially, the compositions of the invention comprise, as adjuvant, one or a number of neutral lipids. Such compositions are particularly advantageous, especially when the ratio R is low. The Applicant has in fact shown that the addition of a neutral lipid makes it possible to improve the formation of the nucleolipid particles and, surprisingly, to promote the penetration of the particle into the cell by destabilizing its membrane.

More preferentially, the neutral lipids used in the context of the present invention are lipids containing 2 fatty chains.

In a particularly advantageous way, use is made of natural or synthetic lipids which are zwitterionic or free of ionic charge under physiological conditions. It can more particularly be chosen from dioleoylphosphatidylethanolamine (DOPE), oleoylpalmitoylphosphatidylethanolamine (POPE), distearoyl-, -palmitoyl- or -mirystoylphosphatidylethanolamine, and their 1 to 3 times N-methylated derivative; phosphatidylglycerols, diacylglycerols, glycosyldiacylglycerols, cerebrosides (such as, especially, galactocerebrosides), sphingolipids (such as, especially, sphingomyelins) or alternatively asialogangliosides (such as, especially, asialoGM1 and asialoGM2).

These various lipids can be obtained either by synthesis or by extraction from organs (example: the brain) or from eggs, by conventional techniques well known to those skilled in the art. In particular, the extraction of natural lipids can be carried out by means of organic solvents (see also Lehninger, Biochemistry).

The compositions of the invention preferentially comprise from 0.1 to 20 equivalents of adjuvant per 1 equivalent of lipopolyamine and, more preferentially, from 1 to 5.

The compositions according to the invention can be formulated for the purposes of topical, cutaneous, oral, rectal, vaginal, parenteral, intranasal, intravenous, intramuscular, subcutaneous, intraocular and transdermal administrations and the like. The pharmaceutical compositions of the invention preferably contain a pharmaceutical vehicle which is acceptable for an injectable formulation, especially for direct injection into the desired organ, or for a topical administration (on the skin and/or mucosal membranes). They can in particular be isotonic, sterile solutions or dry compositions, especially lyophilized, which, by addition, depending on the situation, of sterilized water or of physiological serum, make it possible to prepare injectable solutions. The doses of nucleic acid used for injection, as well as the number of administrations, can be varied according to various parameters, and especially as a function of the method of administration used, of the pathology under consideration, of the gene to be expressed or alternatively of the desired duration of treatment.

The present invention thus provides a particularly advantageous method for the treatment of diseases, comprising the in vivo administration of a nucleic acid capable of correcting the said disease in combination with a lipopolyamine under the conditions defined above. More particularly, this method can be applied to the diseases resulting from a deficiency in a protein or nucleic product and the nucleic acid administered codes for the said protein product or contains the said nucleic product.

The present invention will be more completely described using the following examples, which should be regarded as illustrative and non-limiting.

EXAMPLE 1

Plasmids Used for the In Vivo Gene Transfer

Three types of construction were used for demonstrating the activity of the compositions of the invention: plasmids containing the gene coding for luciferase (Luc), plasmids containing the gene coding for β-galactosidase (LacZ gene) and plasmids containing the gene coding for chloramphenicol acetyltransferase (CAT).

1.1. Plasmids Containing the Luc Gene

The pCMV-luc plasmid contains the promoter of cytomegalovirus (CMV), extracted from the plasmid vector pcDNA3 (Invitrogen) by cutting with the restriction enzymes Mlu I and Hind III, situated upstream of the gene coding for luciferase, inserted at the Mlu I and Hind III sites in the vector pGL basic Vector (Promega).

1.2. Plasmids Containing the LacZ Gene

The pCMV-βGal plasmid (Clontech) contains the CMV promoter situated upstream of the LacZ gene coding for β-galactosidase of Escherichia coli. The pSV-nls LacZ (pAOnlsLacZ) vector contains the same promoter and a nuclear localization sequence (resulting from the SV40 virus) localized in phase and upstream of the LacZ gene. This construction makes possible the expression of the nls-β-galactosidase fusion protein in the nucleus of the cells (cf. De Luze et al., PNAS, 90 (1993), 7322).

1.3. Plasmids Containing the CAT Gene

The plasmids having, for reporter gene, the gene coding for chloramphenicol acetyltransferase (CAT) under the control of RSV (pRSV-CAT) and SV40 (pSV40-CAT) promoters have been published (Boutiller et al., Prog. NeuroPhychoPharmacol. and Biol. Psychiat., 16 (192), 959; de Luze et al., PNAS, 90 (1993), 7322).

EXAMPLE 2

In Vivo Transfer of Nucleic Acid into the Brain of Newborn Mice by Using a Lipopolyamine in a Ratio R=0.8

This example describes the in vivo transfer of the pCMV-luc plasmid into the brain of newborn mice.

30 µg of pCMV-luc plasmid (Example 1.1.) were diluted in 30 µl of 150 mM sterile NaCl (concentration of 1 µg/µl). 0.6 µl of 40 mM dioctadecylamidoglycylspermine (DOGS), prepared in 100% ethanol, were then added.

The mixture was quickly vortexed and used for intracerebral injections in newborn mice. To do this, the mice were anaesthetized by chilling (placed on an aluminium sheet in contact with ice) and then 2 µl of mixture (2 µg of nucleic acid) were injected per mouse. The injections were carried out into the cortex, using a micromanipulator and a microsyringe connected to a microelectrode.

The brains were removed 48 hours later, homogenized and centrifuged and the supernatant was used for quantitatively determining the luciferase. To do this, the supernatant was incubated in the presence of a buffer comprising luciferin, coenzyme A and ATP and the light emitted (generally for 10 seconds) was measured with a luminometer (Wood K. (1990) Promega Notes, 28).

The results obtained show an activity, as standardized relative light units, of 425 RLU/brain (mean of 10 animals) (RLU=relative light unit) when the transfer is carried out by means of the composition according to the invention with R=0.8, against a standardized activity of 100 RLU/brain when the transfer is carried out by means of the plasmid alone (mean of 10 animals).

EXAMPLE 3

Comparison of the in Vivo Transfer of Nucleic Acid into the Brain of Newborn Mice by Using a Lipopolyamine in a Ratio R=1.5 and 0.8

3.1. Transfer of the pCMV-luc Plasmid

For the ratio R=0.8, the conditions are those of Example 2. For the ratio R=1.5, 30 µg of pCMV-luc plasmid (Example 1.1.) were diluted in 30 µl of 150 mm sterile NaCl (concentration of 1 µg/µl). 1.13 µl of 40 mM dioctadecylamidoglycylspermine (DOGS), prepared in 100% ethanol, were then added.

The mixture was quickly vortexed and used for intracerebral injections in newborn mice. To do this, the mice were anaesthetized by cooling (placed on an aluminium sheet in contact with ice) and then 2 µl of mixture (2 µg of nucleic acid) were injected per mouse. The injections were carried out into the cortex, using a micromanipulator and a microsyringe connected to a microelectrode.

The brains were removed 48 hours later, homogenized and centrifuged and the supernatant was used for quantitatively determining the luciferase, according to the procedure described in Example 2. The results obtained show a standardized activity of 89 RLU/brain (mean of 12 animals) when the transfer is carried out by means of the composition of the invention where the ratio R=1.5, against a standardized activity of 100 RLU/brain when the transfer is carried out by means of the composition of the invention with a ratio R=0.8 (mean of 11 animals).

3.2. Transfer of the PSV-nls LacZ Plasmid

The same procedure as in Example 3.1. above was employed for transfecting the pSV-nls LacZ plasmid containing the LacZ gene coding for β-galactosidase under the control of an SV40 (simian virus 40) promoter. This construction (Example 1.2.) also codes for a peptide signalling for nuclear localization. The enzyme β-galactosidase is thus transported towards the nucleus and the enzymatic reaction produced by the nucleic acid is limited to this subcellular region. The injections were carried out in the same way as for the pCMV-luc plasmid and the brains were also removed 48 hours post-transfection, fixed in paraformaldehyde (2%) for 24 hours and then treated for the β-galactosidase reaction. The brains were then examined for expression sites, the positive regions cut in a cryostat (15 mm), mounted on slides and photographed. In 2 independent series of experiments, three animals out of 10 show, in the regions situated around the injection zone, groups of cells in which the nucleus has a very pronounced blue coloration, characteristic of β-galactosidase activity.

EXAMPLE 4

In Vitro Transfer of Nucleic Acids: Optimization of the Lipopolyamine/Adjuvant Ratio This example describes the in vitro transfer of nucleic acids (on cell cultures) by means of a composition according to the invention comprising nucleic acid, a lipopolyamine and an adjuvant (neutral lipid) under various conditions.

$10^5$ cells of the 3T3 fibroblast and HepG2 human hepatoma lines were incubated respectively in the presence of 1 and 2 µg of pCMV-βGal or pCMV-Luc plasmids under various conditions:

in the presence of DOGS in charge ratios R=1 and 1.5 in the absence or in the presence of 1, 2, 5 or 10 equivalents of an adjuvant (DOPE).

The transfecting ability was then determined under the conditions described in Example 2, for luciferase, or by measuring the percentages of cells having a pronounced blue coloration, for the LacZ activity. The results obtained are presented in the tables below.

TABLE 1

| Luciferase activity (as RLU/10 sec/mg Prot.) | | |
|---|---|---|
| Conditions/Cells | 3T3 | HepG2 |
| DOGS (R = 1.5) | $1.7 \times 10^6$ | $2 \times 10^2$ |
| DOGS (R = 1.5) + 2 eq DOPE | $2 \times 10^7$ | $8 \times 10^3$ |

TABLE 2

| | LacZ activity | |
|---|---|---|
| | 3T3 Fibroblasts | |
| DOGS Ratio | 1 | 1.5 |
| 0 eq DOPE | 0 | 5 |
| 1 eq DOPE | 8 | 30 |
| 2 eq DOPE | 48 | 69 |
| 5 eq DOPE | 15 | 25 |
| 10 eq DOPE | 5 | 10 |

EXAMPLE 5

In Vivo Transfer of Nucleic Acid into the Brain of Newborn Mice by Using a Lipopolyamine in a Ratio R=1 and a Neutral Lipid In this example, a 40 mM ethanolic solution of DOGS was mixed with an equal volume of an 80 mM dioleoylphosphatidylethanolamine (DOPE) solution, prepared in a chloroform/ethanol (1/5) mixture. Thus, for one equivalent of DOGS, the composition contains two equivalents of DOPE.

30 µg of pCMV-luc plasmid (Example 1.1.) were diluted in 30 µl of 150 mM sterile NaCl (concentration of 1 µg/µl). 1.5 µl of the DOGS/DOPE mixture prepared above were then added.

The remainder of the procedure (injections, removals, quantitative determinations) is identical to that described in Example 3.1. The results obtained show a standardized activity of 241 RLU/brain (mean of 13 animals) when the transfer is carried out in the presence of the adjuvant (neutral lipid), against a standardized activity of 100 RLU/brain when the transfer is carried out in the presence of DOGS alone, in the same charge ratio R=1 (mean of 13 animals).

EXAMPLE 6

In Vivo Transfer of Nucleic Acid into the Brain of Newborn Mice by Using a Lipopolyamine in a Ratio R=1.25 and a Neutral Lipid In this example, a 40 mM ethanolic DOGS solution was mixed with an equal volume of an 80 mM dioleoylphosphatidylethanolamine (DOPE) solution, prepared in a chlorform/ethanol (1/5) mixture. Thus, for one equivalent of DOGS, the composition contains two equivalents of DOPE.

30 µg of pCMV-luc plasmid (Example 1.1.) were diluted in 30 µl of 150 mM sterile NaCl (concentration of 1 µg/µl). 1.87 µl of the DOGS/DOPE mixture prepared above were then added.

The remainder of the procedure (injections, removals, quantitative determinations) is identical to that described in Example 3.1. The results obtained show a standardized activity of 405 RLU/brain (mean of 8 animals) when the transfer is carried out in the presence of the adjuvant, against a standardized activity of 100 RLU/brain (mean of 8 animals) when the transfer is carried out in the presence of DOGS alone, in the same charge ratio R=1.25.

EXAMPLE 7

In Vivo Transfer of Nucleic Acid into the Brain of Newborn Mice by Using a Lipopolyamine in a Ratio R=1.5 and a Neutral Lipid In this example, a 40 mM ethanolic DOGS solution was mixed with an equal volume of an 80 mM dioleoylphosphatidylethanolamine (DOPE) solution, prepared in a chloroform/ethanol (1/5) mixture. Thus, for one equivalent of DOGS, the composition contains two equivalents of DOPE. 30 µg of pCMV-luc plasmid (Example 1.1.) were diluted in 30 µl of 150 mM sterile NaCl (concentration of 1 µg/µl). 2.26 µl of the DOGS/DOPE mixture prepared above were then added.

The remainder of the procedure (injections, removals, quantitative determinations) is identical to that described in Example 4.1. The results obtained show a standardized activity of 165 RLU/brain (mean of 10 animals) when the transfer is carried out by means of a composition of the invention containing an adjuvant (neutral lipid), against a standardized activity of 100 RLU/brain (mean of 11 animals) when the transfer is carried out by means of DOGS alone, in the same charge ratio (R=1.5).

EXAMPLE 8

In Vivo Transfer of Nucleic Acid in Mice by Using a Lipopolyamine in a Ratio R=3

This example describes the in vivo transfer of the pCMV-luc plasmid on adult mice. The experiments were carried out on adult mice anaesthetized with pentobarbital.

8.1. Transfer by the Venous Route

For each mouse, 100 µg of pCMV-luc plasmid were diluted in 100 µl of 150 mM NaCl. 7.5 µl of 40 mM DOGS were then added to the solution. The jugular vein of the mice was then exposed by dissection and the above solution injected into the jugular in the direction of the heart. The skin was then closed again with clips. 48 hours after injection, the mice were sacrificed by cervical dislocation and the liver, the lungs, the spleen, the brain, the kidneys and a sample of skeletal muscle were removed. After homogenizing and centrifuging, the supernatants were used for quantitatively determining the luciferase. This experiment was carried out on 4 mice. No expression of luciferase was demonstrated in the various tissues tested.

8.2. Transfer by the Intramuscular Route

60 µg of pCMV-luc plasmid were diluted in 300 µl of 150 mM NaCl. 4.5 µl of 40 mM DOGS were then added to the solution. 50 µl of the mixture prepared above (10 µg of DNA) were then injected for each mouse, through the skin, into the anterior tibial muscle. 48 hours after injection, the mice were sacrificed by cervical dislocation and the injected muscles were removed. After homogenizing and centrifuging, the supernatants were used for quantitatively determining the luciferase. This experiment was carried out on 6 mice. No expression of luciferase was detected.

EXAMPLE 9

In Vivo Transfer of Nucleic Acid in Mice by Using a Lipopolyamine in a Ratio R=4

This example describes the in vivo transfer of the pCMV-luc plasmid on adult mice. The experiments were carried out on adult mice anaesthetized with pentobarbital.

9.1. Transfer by the Venous Route

For each mouse, 100 µg of pCMV-luc plasmid were diluted in 100 µl of 150 mM NaCl. 10 µl of 40 mM DOGS were then added to the solution. The jugular vein of the mice was then exposed by dissection and the above solution injected into the jugular in the direction of the heart. The skin was then closed again with clips. 48 hours after injection, the mice were sacrificed by cervical dislocation and the liver, the lungs, the spleen, the brain, the kidneys and a sample of skeletal muscle were removed. After homogenizing and centrifuging, the supernatants were used for quantitatively determining the luciferase. This experiment was carried out on 4 mice. No expression of luciferase was demonstrated in the various tissues tested.

9.2. Transfer by the Intramuscular Route

60 µg of pCMV-luc plasmid were diluted in 300 µl of 150 mM NaCl. 6 µl of 40 mM DOGS were then added to-the solution. 50 µl of the mixture prepared above (10 µg of DNA) were then injected for each mouse, through the skin, into the anterior tibial muscle. 48 hours after injection, the mice were sacrificed by cervical dislocation and the injected muscles were removed. After homogenizing and centrifuging, the supernatants were used for quantitatively determining the luciferase. This experiment was carried out on 6 mice. No expression of luciferase was detected.

What is claimed is:

1. A composition effective for in vivo transfection of a nucleic acid to a cell comprising the nucleic acid and a lipopolyamine, wherein the ratio (R) of positive charges of said lipopolyamine to negative charges of said nucleic acid is less than 2.

2. The composition of claim 1, wherein the nucleic acid is a deoxyribonucleic acid.

3. The composition of claim 1, wherein the nucleic acid is a ribonucleic acid.

4. The composition of claim 1, comprising a carrier that is pharmaceutically acceptable for an injectable formulation.

5. The composition of claim 1, comprising a carrier that is pharmaceutically acceptable for an application on the skin or mucosal membranes.

6. A method for in vivo transfection of cells comprising administering to said cells the composition of claim 1 wherein said composition of claim 1 enhances the in vivo transfection of a nucleic acid to a cell as compared to an in vivo transfection of a nucleic acid using a second composition comprising a nucleic acid and a lipopolyamine, wherein in said second composition, the ratio (R) of positive charges of said lipopolyamine to negative charges of said nucleic acid is greater than or equal to 2.

7. The composition of claim 1, wherein the nucleic acid is an antisense.

8. The composition of claim 1, wherein the nucleic acid contains a gene encoding a protein product.

9. The composition of claim 1, wherein the ratio R is between 0.1 and 1.9.

10. The composition of claim 9, wherein the ratio R is between 0.5 and 1.5.

11. A composition effective for in vivo transfection of a nucleic acid to a cell comprising the nucleic acid, a lipopolyamine and an adjuvant effective for combining with a lipopolyamine/nucleic acid complex and for improving its transfecting ability, wherein the ratio (R) of positive charges of said lipopolyamine to negative charges of said nucleic acid is less than 2.

12. The composition of claim 11, wherein the adjuvant comprises a neutral lipid.

13. The composition of claim 11, wherein the neutral lipid is a synthetic or natural lipid that is zwitterionic or free of ionic charge under physiological conditions.

14. The composition of claim 12, wherein the neutral lipid comprises two fatty chains.

15. The composition of claim 13, wherein the neutral lipid is selected from the group consisting of dioleoylphosphatidylethanolamine (DOPE), oleoylpalmitoylphosphatidylethanolamine (POPE), distearoylphosphatidylethanolamine, dipalmitoylphosphatidylethanolamine, dimirystoylphosphatidylethanolamine, phosphatidylglycerols, diacylglycerols, glycosyldiacylglycerols, cerebrosides, sphingolipids and asialogangliosides.

16. The composition of claim 11, comprising from 0.1 to 20 equivalents of adjuvant per 1 equivalent of lipopolyamine.

17. The composition of claim 15, wherein the cerebrosides are galactocerbrosides.

18. The composition of claim 15, wherein the sphingolipids are sphingomyelins.

19. The composition of claim 15, wherein the asialogangliosides are asialoGM1, asialoGM2, or both asialoGM1 and asialoGM2.

20. The composition of claim 16, comprising from 1 to 5 equivalents of adjuvant per 1 equivalent of lipopolyamine.

21. A method for in vivo transfection of cell comprising administering to said cells the composition of claim 11, wherein said composition of claim 11 enhances the in vivo transfection of a nucleic acid to a cell as compared to an in vivo transfection of a nucleic acid using a second composition comprising a nucleic acid, a lipopolyamine, and an adjuvant, wherein in said second composition, the ratio (R) of positive charges of said lipopolyamine to negative charges of said nucleic acid is greater than or equal to 2.

22. A composition effective for in vivo transfection of a nucleic acid to a cell comprising the nucleic acid and a lipopolyamine, wherein the ratio (R) of positive charges of said lipopolyamine to negative charges of said nucleic acid is less than 2 and wherein the lipopolyamine comprises a hydrophilic polyamine region of formula $H_2N-(-(CH_2)_m-NH)_n-H$ in which m is an integer greater than or equal to 2, m is the same or different between different carbon groups included between two amines, n is an integer greater than or equal to 1, and the lipopolyamine further comprises a lipophilic region selected from the group consisting of saturated hydrocarbon chain, unsaturated hydrocarbon chain, cholesterol, and a synthetic lipid that forms lamellar or hexagonal phases.

23. The composition of claim 1 wherein m is between 2 and 6 inclusive and n is between 1 and 5 inclusive.

24. The composition of claim 2, wherein the ratio R is between 0.1 and 1.9.

25. The composition of claim 24, wherein the ratio R is between 0.5 and 1.5.

26. The composition of claim 22, wherein the nucleic acid and the lipopolyamine associate to form a lipopolyamine/nucleic acid complex.

27. The composition of claim 26, further comprising an adjuvant that associates with the lipopolyamine/nucleic acid complex and improves the composition's transfecting ability.

28. The composition of claim 27 wherein the adjuvant is a neutral lipid.

29. The composition of claim 27, wherein the adjuvant is selected from the group consisting of dioleoylphosphatidylethanolamine (DOPE), oleoylpalmitoylphosphatidylethanolamine (POPE), distearoylphosphatidylethanolamine, dipalmitoylphosphatidylethanolamine, dimirystoylphosphatidylethanolamine, phosphatidylglycerols, diacylglycerols, glycosyldiacylglycerols, cerebrosides, sphingolipids and asialogangliosides.

30. A method for in vivo transfection of cells comprising administering to said cells the composition of claim 27, wherein said composition of claim 27 enhances the in vivo transfection of a nucleic acid to a cell as compared to an in vivo transfection of a nucleic acid using a second composition comprising a nucleic acid, a lipopolyamine, and an adjuvant, wherein in said second composition, the ratio (R) of positive charges of said lipopolyamine to negative charges of said nucleic acid is greater than or equal to 2.

* * * * *